(12) United States Patent
Martella

(10) Patent No.: US 6,332,885 B1
(45) Date of Patent: Dec. 25, 2001

(54) SYNTHESIS DEVICE FOR ORTHOPAEDIA AND TRAUMATOLOGY

(76) Inventor: Pasquale Martella, Via Certosa, 3, 35010 Vigodarzere (IT)

(*) Notice: Subject to any disclaimer, the term of this patent is extended or adjusted under 35 U.S.C. 154(b) by 0 days.

(21) Appl. No.: 09/703,633

(22) Filed: Nov. 2, 2000

Related U.S. Application Data

(63) Continuation of application No. PCT/IB99/00801, filed on May 4, 1999.

(51) Int. Cl.⁷ .................................................. A61B 17/86
(52) U.S. Cl. ................................. 606/78; 606/69; 606/72
(58) Field of Search ..................... 606/60, 61, 62, 606/63, 67, 68, 69, 70, 72, 73, 75, 76, 78, 151, 155, 213, 232

(56) References Cited

U.S. PATENT DOCUMENTS

| | | | |
|---|---|---|---|
| 5,584,695 | 12/1996 | Sachdeva et al. | 433/173 |
| 5,697,779 | * 12/1997 | Sachdeva et al. | 433/2 |
| 5,893,856 | * 4/1999 | Jacob et al. | 606/151 |
| 5,951,288 | * 9/1999 | Sawa | 433/173 |

FOREIGN PATENT DOCUMENTS

| | | |
|---|---|---|
| A-2 727 304 | 5/1996 | (FR) . |
| A-1 147 378 | 3/1985 | (RU) . |

\* cited by examiner

*Primary Examiner*—David O. Reip
(74) *Attorney, Agent, or Firm*—Guido Modiano; Albert Josif; Daniel O'Byrne

(57) ABSTRACT

The device according to the invention is composed of an axially perforated cylinder having at least one split end so as to form at least two independent sectors. The material of which the cylinder is made is a Ni—Ti alloy with hot, cold or superelastic shape memory. The cylinder is inserted in a hole that passes through the fracture region and is heated with an electric scalpel, causing the independent sectors of the split end to open out and accordingly compact and couple the two fractured segments.

8 Claims, 4 Drawing Sheets

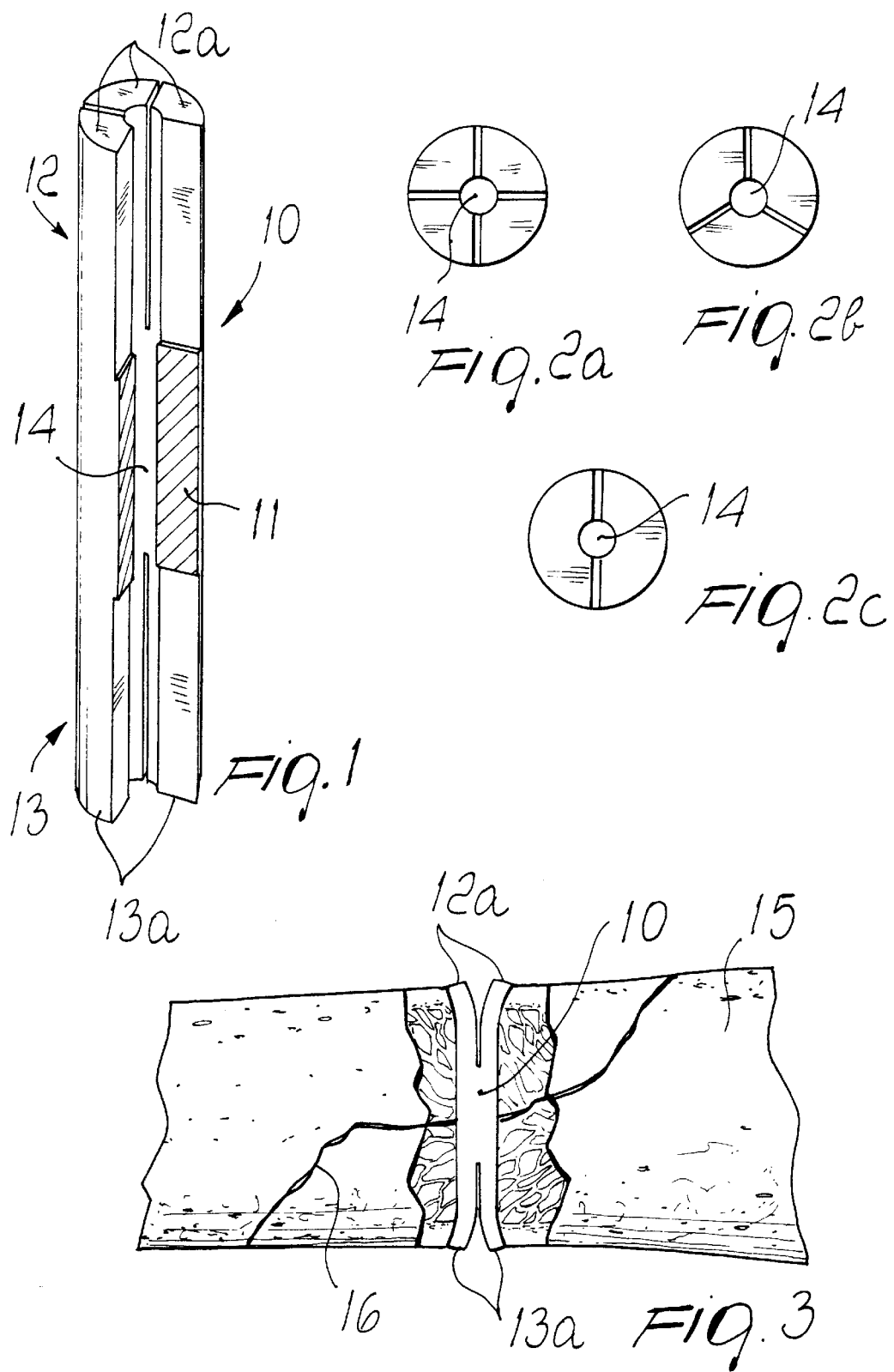

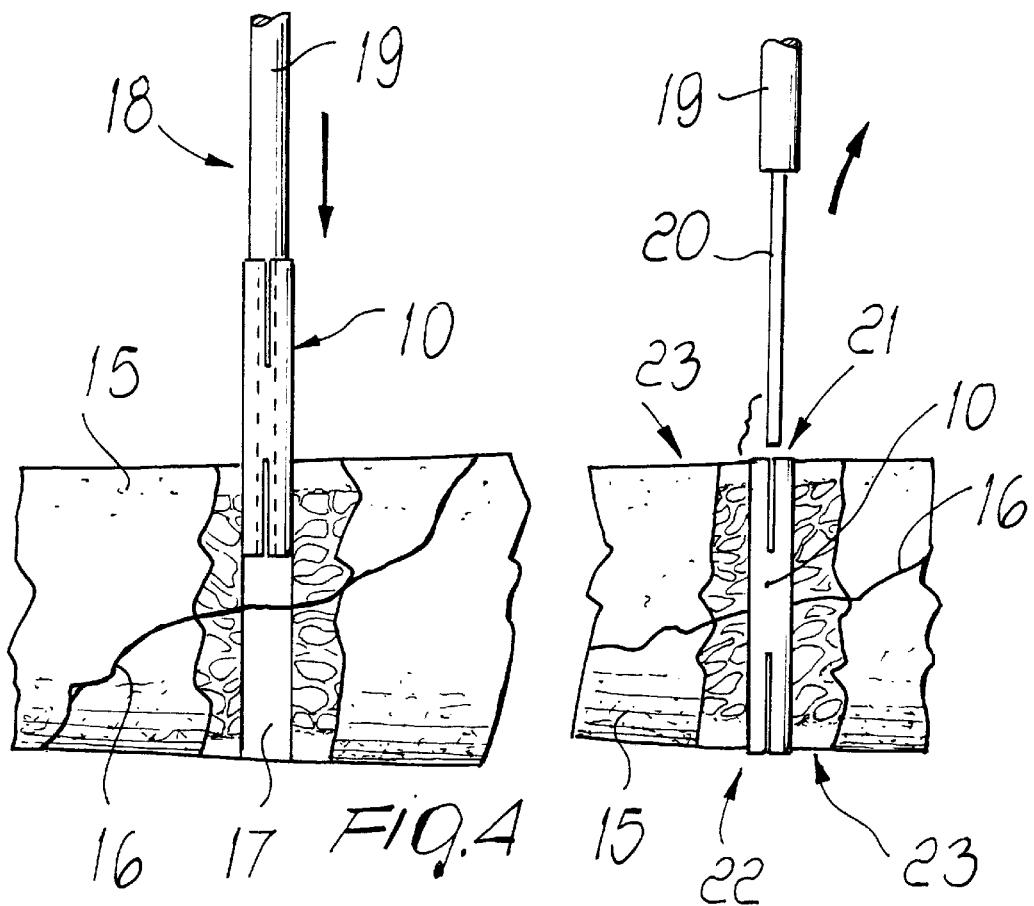
Fig.4
Fig.5
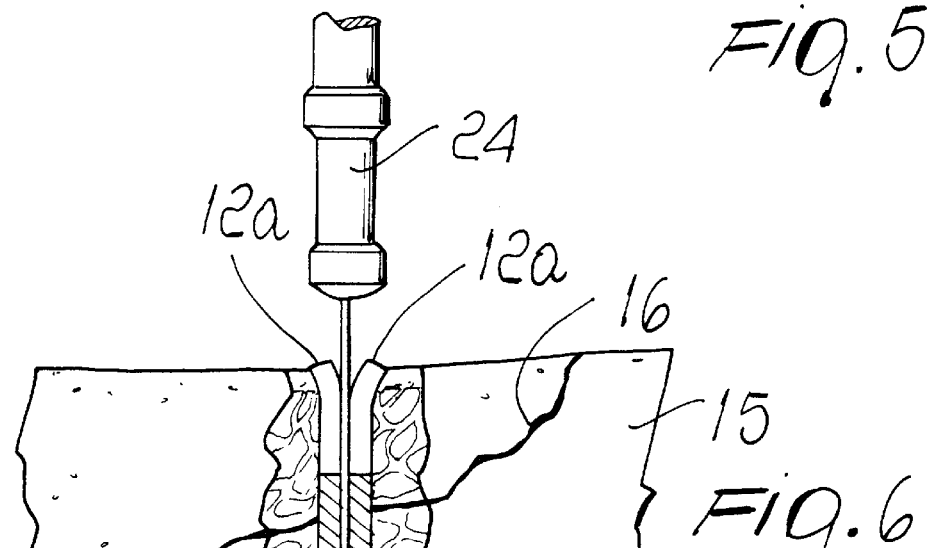
Fig.6

SYNTHESIS DEVICE FOR ORTHOPAEDIA AND TRAUMATOLOGY

CROSS-REFERENCE TO RELATED APPLICATIONS

This application is a continuation of application Ser. No. PCT/IB99/00801 filed on May 4, 1999.

BACKGROUND OF THE INVENTION

The present invention relates to a synthesis device for orthopaedia and traumatology.

More particularly, the present invention relates to a device for the synthesis of a bone fracture after its reduction by means of a body which allows to fix the fractured region, keeping it in the correct position for the time required by the bone to strengthen.

Various devices used to perform this operation are known.

Among these, the devices most frequently used are screws of the self-tapping or through type, possibly cooperating with plates which are arranged laterally to the bone in the region where the fracture is present.

All these devices are very troublesome to position and also have problems linked, among other issues, to the compactness of the bone in the fractured region.

More particularly, screws of the self-tapping type rely on a good grip of the thread, but this does not always occur.

Through screws associated with external plates are very bulky and must usually be removed when the bone has consolidated in the fracture region.

Substantially U-shaped brackets are also known which are made of materials having shape memory; their wings are inserted in two holes formed in the bone on opposite sides with respect to the fracture line.

These brackets, when heated, shorten in the intermediate region between the two ends inserted in the bone or the two ends bend toward each other, connecting the fracture.

However, these brackets have the drawback that they act only by traction in the external cortical region of the bone and in many cases do not allow to control the fracture region and keep it in the correct position.

U.S. Pat. No. 5,584,695 discloses an apparatus for anchoring a prosthetic tooth 21 to a patient's jawbone 22 including a root screw 26, with a longitudinal bore 29, for implantation in the jawbone 22, and a temperature-sensitive shape-memory cylindrical coupling pin 34 for fixing a stump 35, with its own longitudinal bore 39 and mounting the prosthetic tooth 21, to the root screw 26. The coupling pin 34 extends into the aligned bores 29 and 39, and at temperatures below its transformation temperature range (TTR) the coupling pin 34 is thinner than the diameters of such bores 29 and 39 for easy insertion and extraction therefrom, while at temperatures above its TTR the coupling pin 34 expands inside the bores 29 and 39 to lock the mounting stump 35 to the root screw 26. In one specific embodiment (FIG. 2C), the cylindrical coupling pin 34 has a forked end portion 47 with two or more prongs 48 which open up at temperatures above the TTR for locking the coupling pin 34 into either or both bores 29 and 39.

FR-A-2727304 discloses a self-locking medullary canal bone implant having at least one section made from a metal alloy with a shape memory effect, situated at one or both ends or along its whole length. The implant is shaped for convenient positioning and its shape changes on heating or cooling so that it grips the inside of the bone and holds firmly in place.

SUMMARY OF THE INVENTION

The aim of the present invention is to provide a synthesis device for orthopaedia and traumatology which can advantageously overcome the described problems.

A consequent primary object is to pprovide a device which can be easily inserted in the fracture region and is capable of keeping the fractured region correctly aligned.

Another object is to provide a synthesis device which, once inserted, can compact the fracture region.

Another object is to provide a synthesis device which has small dimensions, so that it can be left in the bone also after said bone has consolidated in the fracture region.

In accordance with the invention, there is provided a synthesis device for orthopaedia and traumatology as defined in the appended claims.

BRIEF DESCRIPTION OF THE DRAWINGS

Further characteristics and advantages of the invention will become apparent from the description of some embodiments thereof, illustrated only by way of non-limitative example in the accompanying drawings, wherein:

FIG. 1 is a partial sectional view of the device according to the invention;

FIGS. 2a, 2b and 2c are views of three types of the same device with a different number of sectors of the end parts;

FIG. 3 is a view of the individual synthesis device installed to lock a region after reduction of the fracture;

FIG. 4 is a view of the insertion of the device of FIG. 3 by means of an auxiliary guiding tool;

FIG. 5 is a view of the correct positioning of the device and of the extraction of the auxiliary guiding tool;

FIG. 6 is a view of the activation of the device by means of an electric scalpel;

DESCRIPTION OF THE PREFERRED EMBODIMENTS

Figure 7:
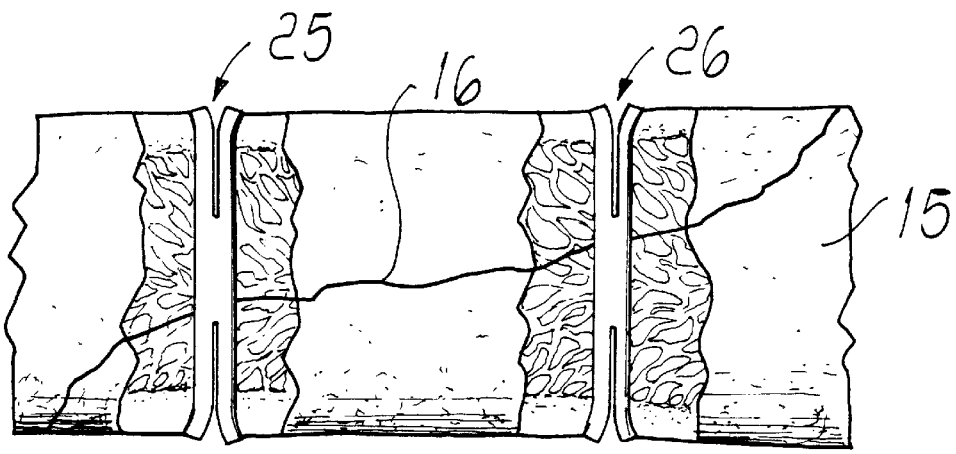
FIG. 7 is a view of the arrangement of two devices in an extensive fracture.

With reference to the above figures, the synthesis device according to the invention is composed of a cylindrical body, generally designated by the reference numeral 10, which has a median region 11 and two end regions 12 and 13.

In the illustrated embodiment, each one of the end regions 12 and 13 is divided into sectors, respectively 12a and 13a, which are divided along diametrical planes.

The entire cylinder is crossed by an axial hole designated by the reference numeral 14.

FIGS. 2a, 2b and 2c illustrate different shapes of the end regions, respectively divided into 4, 3 and 2 sectors; the axial hole 14 is always provided in each case.

The synthesis device is made of a Ni—Ti alloy with thermoelastic transformation and shape memory.

Substantially, the device is produced with a shape which is different from the one shown in FIG. 1 and is given to said cylinder with a known technology.

The cylinder has a memory of the previous shape which is known as:
- hot memory, when the split end begins to open out at 35° C., stops opening at 55° C. and malleability occurs at 20° C.;
- cold memory, when the split end begins to open out at 20° C., stops opening at 35° C. and malleability occurs at 10° C.

Due to the above-defined temperatures, the sectors of the split end return to the memorized shape, which is then maintained.

FIG. 3 illustrates the device in position for compacting a fractured region of a bone 15, wherein the already-reduced fracture line is designated by the reference numeral 16.

The operations for placing the synthesis device are shown in FIGS. 4, 5 and 6.

After reducing the fracture, whose line is again designated by the reference numeral 16, the bone being again designated by the reference numeral 15, a through hole 17 is formed and the device 10 is inserted by means of an auxiliary guiding tool 18 which is constituted by a handle body 19 which has, at its end, a needle 20 which has a slightly smaller diameter than the hole 14 that passes through the device 10.

With this auxiliary guiding tool it is possible to insert the device in the hole 17 as shown in FIG. 5.

The length of the device is chosen so as to be slightly greater than the length of the bone in the fractured region, so that its ends, designated by the reference numerals 21 and 22, protrude by approximately 2 mm from the outer cortical region of the bone, designated by the reference numeral 23.

The end of an electric scalpel 24 is then inserted in the hole 14 as shown in FIG. 6.

The heating produced by the electric scalpel causes the device to return to the memorized shape, opening out the sectors 12a and 13a with a particularly large spacing in the end regions.

In this way, in addition to maintaining the reduction of the fracture for the insertion of the device, compression of the two segments of the bone at the fracture line is also achieved.

Conveniently, the device has a diameter of approximately 3 mm, with an axial hole of 1 mm, but these dimensions, as well as the length, can differ according to requirements.

FIG. 7 illustrates a reduction of an extensive fracture by means of two. synthesis devices, now generally designated by the reference numerals 25 and 26, while the bone is again designated by the reference numeral 15 and the fracture line is again designated by the reference numeral 16.

Figure 8:
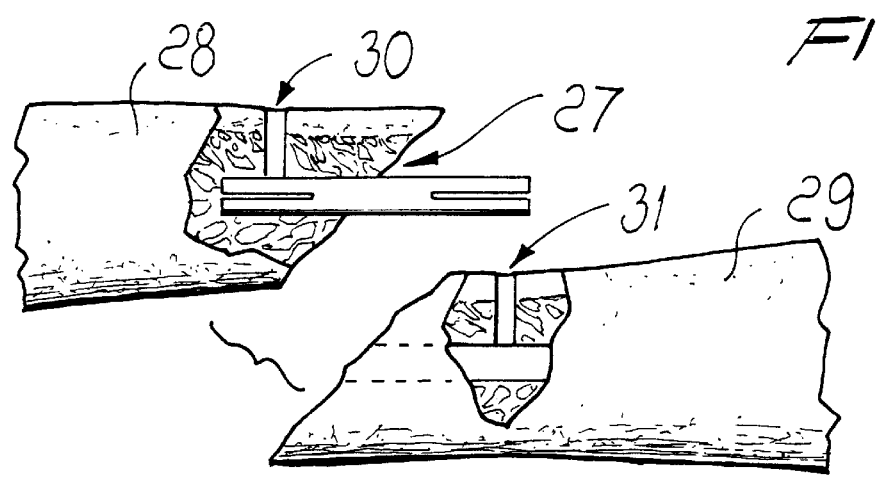
FIG. 8 is a view of a step of the insertion of the device with intramedullary placement.
Figure 9:
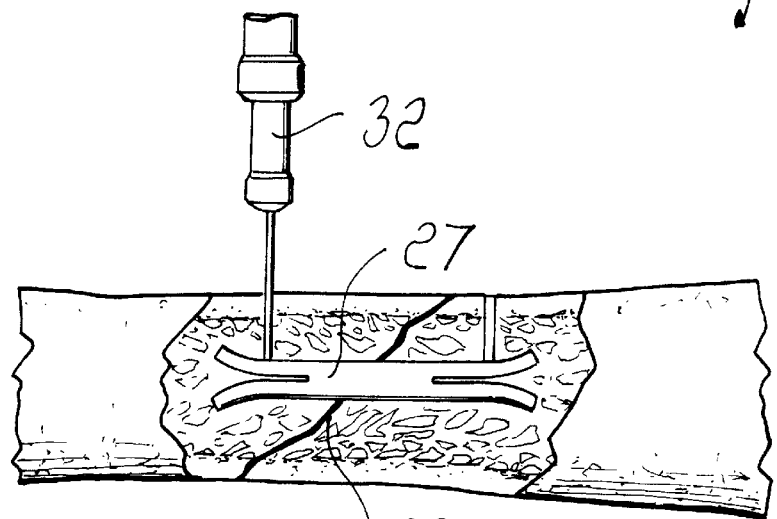
FIG. 9 is a view of the activation of the device of FIG. 8.

FIGS. 8 and 9 illustrate the synthesis device fitted in an intramedullary manner.

In this case, the device, now designated by the reference numeral 27, is first placed on one fractured bone segment, designated by the reference numeral 28, while the second segment, designated by the reference numeral 29, is displaced in order to allow the operation.

The second segment 29 is then moved into its correct position, so that the synthesis device 27 is in an intramedullary position.

Two holes, designated by the reference numerals 30 and 31 respectively, are formed beforehand in the two segments and are located at the two ends of the device 27.

After reducing the fracture as shown in FIG. 9, the electric scalpel, now designated by the reference numeral 32, is inserted; said scalpel heats and causes the spacing of the end sectors of the synthesis device 27.

Also in this case, by way of said spacing the fracture line, now designated by the reference numeral 33, is compressed.

Figure 10:
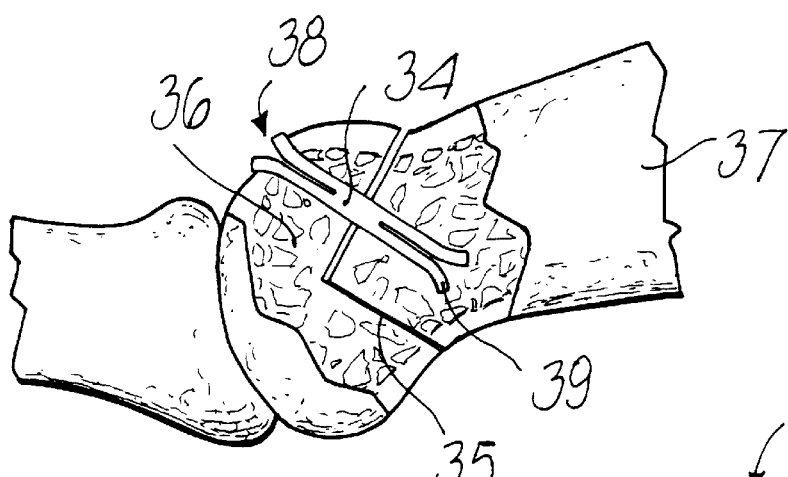
FIG. 10 is a view of the device used for Austin osteotomy of the first metatarsus.
Figure 11:
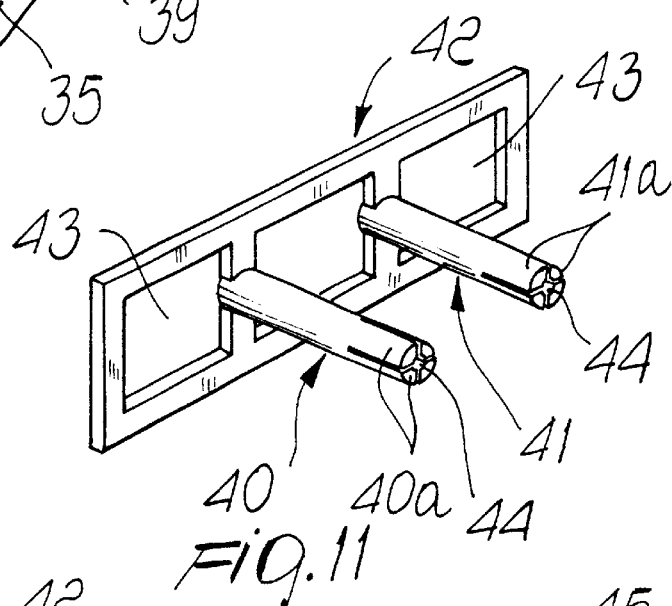
FIG. 11 is a view of two cylinders associated with a flat frame.
Figure 12:
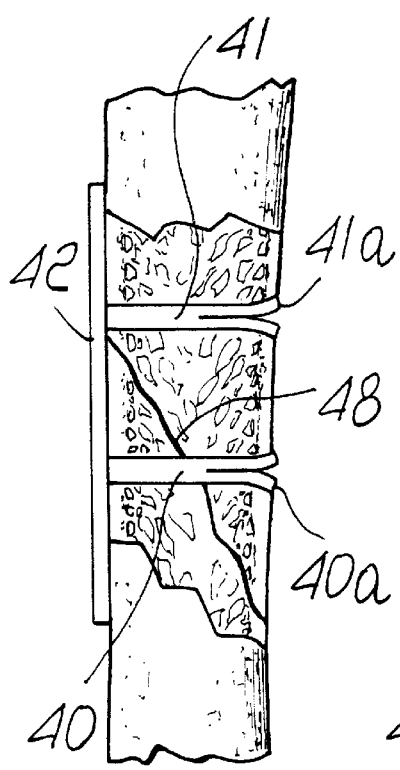
FIG. 12 is a view of the connection of the device of FIG. 11 for reducing a fracture.
Figure 13:
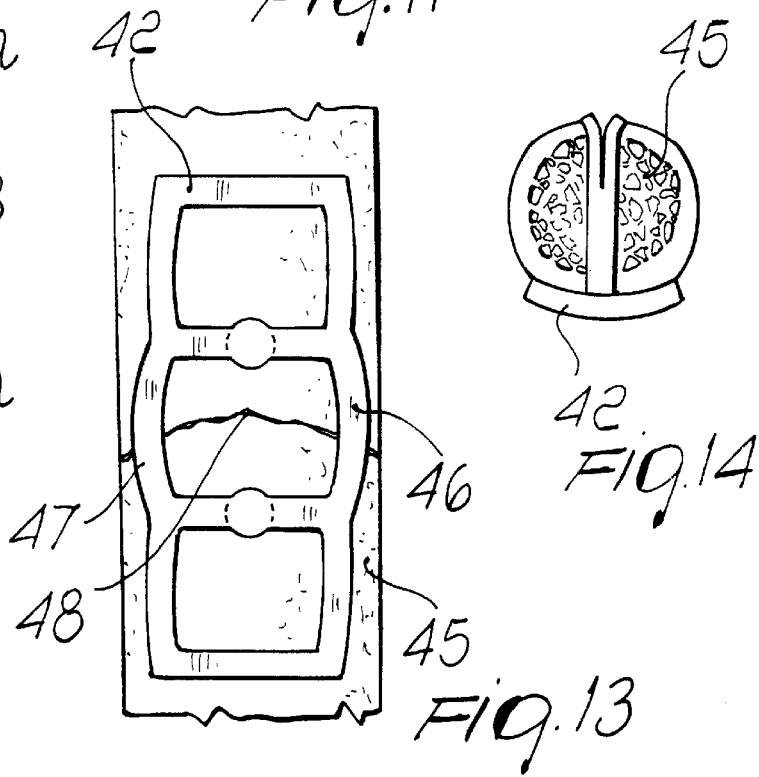
FIG. 13 is a front view of the deformation of the flat frame with shortening of the center distance between the two cylinders.

FIG. 10 illustrates the use of the synthesis device, now designated by the reference numeral 34, for Austin osteotomy of the first metatarsus.

In this case, after producing a cut, with a known technique, along the broken line 35 and after correctly positioning the two bone parts 36 and 37, a blind hole is formed and the synthesis device 34 is inserted therein.

Heating by means of an electric scalpel allows the sectors, now designated by the reference numeral 38, to open out on the outer cortex and allows the sectors of the other end, now designated by the reference numeral 39, to open out in the spongy region of the head.

FIGS. 11, 12, 13 and 14 illustrate a synthesis device which constitutes a different embodiment of the inventive concept.

In this case, two cylinders, now designated by the reference numerals 40 and 41, are associated at right angles with a flat frame 42 which has perforated regions 43.

The two cylinders 40 and 41 have free ends which are again divided into sectors, now designated by the reference numerals 40a and 41a, and there is again an axial hole designated by the reference numeral 44.

The entire unit is monolithic and again made of the same alloy having shape memory.

Figure 14:
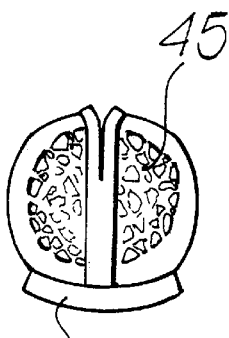
FIG. 14 is a view of the curved shape assumed by the flat frame after heating.

In this case, the memorized shape is such that heating, again performed by means of an electric scalpel, in addition to opening out the end sectors 40a and 41a of the cylinders 40 and 41, also bends the flat frame as shown in FIG. 14, so as to adapt to the rounded shape of the bone, now designated by the reference numeral 45.

The flat frame again changes shape, curving the two connections 46 and 47 and thus tending to move the cylinders 40 and 41 mutually closer.

This produces the compression of the fracture line designated by the reference numeral 48.

From the description and the illustrations it is evident that the intended aim and all of the objects have been achieved.

The new synthesis device for orthopaedia and traumatology is very simple and easy to install.

Once the fracture or osteotomy has been reduced, the bone is prepared as if to place a screw and then the metal cylinder is inserted, with the suitable guiding tool as shown, in the hole prepared beforehand.

It is then sufficient to insert an electric scalpel in the axial hole of the cylinder to open out the sectors and/or deform the plate.

After the installation and opening out of the device, optimum and prolonged compression between the fragments is provided.

The compression force can vary between 3 and 5 kg depending on the diameter and length of the metal cylinder.

As mentioned, the device can be used as a means for intramedullary synthesis.

In this case, the sectors that open out grip the internal cortex.

The main recommendations for the use of the synthesis device are fractures and osteotomies of the metatarsi and metacarpi, arthrodeses of the interphalangeal articulations through an intramedullary pathway, arthrodeses of the first metatarsal-phalangeal joint, clavicular fractures through an intramedullary pathway, Austin osteotomy of the first metatarsus, etcetera.

The main indications for using the device provided with a flat frame are fractures of the distal diaphysis and epiphysis of the radium, ulnar fractures, clavicular fractures, etcetera.

The embodiments may obviously be different as convenient starting from the same inventive concept and always using a material with shape memory.

The disclosures in Italian Patent Application No. PD98A000110 from which this application claims priority are incorporated herein by reference.

What is claimed is:

1. A synthesis device for orthopaedia and traumatology, comprising a cylinder which is made of a Ni—Ti alloy having shape memory, at least one of two ends of said cylinder being split outwardly openable by heating, assuming a memorized shape and maintaining said memorized shape after cooling, said cylinder having a chosen length such that when inserted in a through hole traversing a fracture line of a fractured region of a bone said at least one of the two ends protrudes by a short extent from an outer cortical region of the bone so that said split outwardly opening by heating produces a compaction and coupling of two fracture segments of said fractured region of the bone, said cylinder having a median region which continues with two end regions which are split and divided into a plurality of sectors, an axial hole being provided for insertion of a heating electric scalpel.

2. The synthesis device according to claim 1, wherein the Ni—Ti alloy has hot memory and an opening out of the split at least one end begins at approximately 35° C., ends at approximately 55° C., and malleability occurs at approximately 20° C.

3. The synthesis device according to claim 1, wherein the Ni—Ti alloy has cold memory and an opening out of the split at least one end begins at approximately 20° C., ends at approximately 35° C., and malleability occurs at approximately 10° C.

4. The synthesis device according to claim 1, wherein the chosen length of said cylinder is such that two ends of said cylinder protrude by a short extent from the outer cortical region of the bone so that said split outwardly opening by heating produces the compaction and coupling of the two fracture segments.

5. The synthesis device according to 1, wherein said ends of the cylinder are divided into four sectors.

6. A synthesis device for orthopaedia and traumatology, comprising at least two cylinders each with one end which is divided into sectors and another end which is associated at right angles with a plate which is perforated so as to form a frame, the device being entirely made of a same shape-memory alloy, said sectors of said cylinders opening out due to heating and said frame shortening in a region between the cylinders in order to compact a fracture region and bending as a whole toward the cylinders in order to assume a shape which adapts to a shape of a bone to which said device is applied.

7. A method for compacting a fractured region of a bone, comprising the steps of:

providing a through hole traversing a fracture line of the fractured region of the bone;

providing a synthesis device comprising a cylinder made of a Ni—Ti alloy having shape memory and having two ends at least one of which being split outwardly openable by heating so as to assume a memorized shape and maintain said memorized shape after cooling;

inserting said synthesis device through said through hole such that said at least one of the two ends protrudes by a short extent from an outer cortical region of the bone so that said split outwardly opening by heating produces a compaction and coupling of two fracture segments of said fractured region of the bone.

8. The method of claim 7, comprising inserting said synthesis device through said through hole such that both said two ends protrude by a short extent from a respective outer cortical region of the bone so that said split outwardly opening by heating produces a compaction and coupling of two fracture segments of said fractured region of the bone.

* * * * *

UNITED STATES PATENT AND TRADEMARK OFFICE
CERTIFICATE OF CORRECTION

PATENT NO.     : 6,332,885 B1                                                Page 1 of 1
DATED          : December 25, 2001
INVENTOR(S)    : Pasquale Martella It is certified that error appears in the above-identified patent and that said Letters Patent is hereby corrected as shown below:

<u>Title page,</u>
Insert Item -- [30] Foreign Application Priority Data
        May 7, 1998    [IT] ........................ PD98A000110 --

Signed and Sealed this

Fourth Day of May, 2004

JON W. DUDAS
*Acting Director of the United States Patent and Trademark Office*